US007207970B2

(12) United States Patent
Hasegawa

(10) Patent No.: US 7,207,970 B2
(45) Date of Patent: Apr. 24, 2007

(54) DISPLACEABLE-PLUG-CONTAINING FILLING/DISCHARGING PORT AND MEDICAL CONTAINER HAVING THE SAME

(75) Inventor: Mitsuru Hasegawa, Osaka (JP)

(73) Assignee: Nipro Corporation, Osaka (JP)

( * ) Notice: Subject to any disclaimer, the term of this patent is extended or adjusted under 35 U.S.C. 154(b) by 350 days.

(21) Appl. No.: 10/875,737

(22) Filed: Jun. 25, 2004

(65) Prior Publication Data

US 2005/0075613 A1 Apr. 7, 2005

(30) Foreign Application Priority Data

Jun. 27, 2003 (JP) ............................ 2003-185662

(51) Int. Cl.
*A61M 5/19* (2006.01)
*A61M 5/148* (2006.01)
*B65D 25/08* (2006.01)

(52) U.S. Cl. ........................ 604/90; 604/408; 604/410; 604/416; 206/221

(58) Field of Classification Search ................ 604/408, 604/257, 409, 410, 416, 903, 89, 90, 91; 206/221
See application file for complete search history.

(56) References Cited

U.S. PATENT DOCUMENTS 2,435,637 A * 2/1948 Wolf .......................... 604/408
2,533,806 A * 12/1950 Holzapfel .................. 206/221
2,665,690 A * 1/1954 Lockhart .................... 206/221
2,695,614 A * 11/1954 Lockhart .................... 206/221
2,756,874 A * 7/1956 Erickson et al. ............ 206/221
2,781,141 A * 2/1957 Lucien ....................... 206/221
2,808,829 A * 10/1957 Butler ........................ 604/262
2,894,510 A * 7/1959 Bellamy, Jr. ................ 604/408
2,916,197 A * 12/1959 Lingenfelter et al. ....... 206/219
3,144,151 A * 8/1964 Grass ......................... 206/221
3,198,194 A * 8/1965 Wilburn ..................... 206/221
3,537,605 A * 11/1970 Solowey ..................... 206/222
3,563,415 A * 2/1971 Ogle ....................... 222/145.4
3,651,990 A * 3/1972 Cernei ......................... 222/94
3,838,689 A * 10/1974 Cohen .......................... 604/90
3,885,710 A * 5/1975 Cohen ........................ 222/129
3,924,741 A * 12/1975 Kachur et al. ............. 206/221

(Continued)

FOREIGN PATENT DOCUMENTS

GB 2 309 681 A 8/1997

(Continued)

*Primary Examiner*—Tatyana Zalukaeva
*Assistant Examiner*—Paula L Craig
(74) *Attorney, Agent, or Firm*—Kubovcik & Kubovcik

(57) ABSTRACT

A filling/discharge port 10 which includes a port cap 20, a plug 40 which is slidably fitted in the inside of the port cap 20, and a plug cap 50 which is removably fitted to the tip of the plug 40 is provided for use in a liquid medicament containing chamber 563 of a container body 560 which is partitioned into a plurality of chambers 562 and 563 via a partitioning portion 561 which allows communication when the internal pressure of the container body 560 is increased, and the plug 40 is slidable from a closed position to a discharge position owing to an increase in the internal pressure. The filling/discharge port 10 reliably prevent medicaments in a medical container which contains a plurality of medicaments from being administered to a patient without being mixed so that they can be mixed during use.

7 Claims, 9 Drawing Sheets

U.S. PATENT DOCUMENTS

| | | | | | |
|---|---|---|---|---|---|
| 3,974,938 | A | | 8/1976 | Steadman | 220/266 |
| 3,994,412 | A | * | 11/1976 | Difiglio | 220/266 |
| 4,172,457 | A | * | 10/1979 | Choksi et al. | 604/92 |
| 4,187,893 | A | * | 2/1980 | Bujan | 604/408 |
| 4,402,434 | A | * | 9/1983 | Baker | 222/492 |
| 4,458,733 | A | * | 7/1984 | Lyons | 141/1 |
| 4,550,825 | A | * | 11/1985 | Sutryn et al. | 206/222 |
| 4,608,043 | A | * | 8/1986 | Larkin | 604/87 |
| 4,614,267 | A | * | 9/1986 | Larkin | 206/221 |
| 4,950,237 | A | * | 8/1990 | Henault et al. | 604/82 |
| 4,979,648 | A | * | 12/1990 | Montgomery et al. | 222/153.14 |
| 5,125,921 | A | * | 6/1992 | Duschek | 604/415 |
| 5,246,142 | A | * | 9/1993 | DiPalma et al. | 222/129 |
| 5,395,325 | A | * | 3/1995 | Moreno et al. | 604/89 |
| 5,405,333 | A | | 4/1995 | Richmond | 604/257 |
| 5,462,526 | A | * | 10/1995 | Barney et al. | 604/85 |
| 5,554,134 | A | * | 9/1996 | Bonnichsen | 604/240 |
| 5,632,906 | A | * | 5/1997 | Ishida et al. | 210/787 |
| 5,875,889 | A | * | 3/1999 | Albisetti | 206/221 |
| 5,944,709 | A | * | 8/1999 | Barney et al. | 604/410 |
| 6,170,654 | B1 | * | 1/2001 | Gartner et al. | 206/219 |
| 6,544,213 | B1 | * | 4/2003 | Lifshey | 604/89 |
| 6,758,359 | B2 | * | 7/2004 | Yurkewicz et al. | 215/251 |
| 2001/0047162 | A1 | * | 11/2001 | Yugari | 604/410 |
| 2002/0066715 | A1 | * | 6/2002 | Niedospial, Jr. | 215/311 |
| 2003/0105448 | A1 | * | 6/2003 | Shiraishi et al. | 604/415 |
| 2005/0087456 | A1 | * | 4/2005 | Oka et al. | 206/219 |

FOREIGN PATENT DOCUMENTS

| | | |
|---|---|---|
| JP | 8-257102 A | 10/1996 |
| JP | 9-327498 | 12/1997 |

* cited by examiner

DISPLACEABLE-PLUG-CONTAINING FILLING/DISCHARGING PORT AND MEDICAL CONTAINER HAVING THE SAME

BACKGROUND OF THE INVENTION

The present invention relates to a filling/discharge port of a medical container and a medical container having the same. More specifically, the present invention relates to a filling/discharge port in which a displaceable plug is fitted as well as to a medical container having the filling/discharge port, which contains a plurality of medicaments to be mixed in use.

BACKGROUND ART

In recent years, a medical container that contains plural chambers containing medicaments unstable in their mixed state and separated via a partitioning portion which allows communication therebetween during use has been well known. One example is a so-called "plural-chamber bag" which is a soft-bag-type medical container made of thermoplastic resin sheets. A partitioning portion between a chamber which contains a liquid medicament or a dissolving solution and a chamber which contains a powdered medicament is formed as a weakly sealed portion which is opened by pressure caused by pressing the outside of the chamber which contains the liquid medicament (Japanese unexamined publication patent No. 8-257102). This plural-chamber bag has the advantages that the bag is lightweight and is not easily broken during transportation, that space of its safekeeping place can be saved, that operation efficiency of medical operators is improved, and that its individual members need not be separately discarded.

All currently marketed plural-chamber bags which contain a liquid medicament and a powdered medicament have a filling/discharge port in a medical liquid-containing chamber. Since a powdered medicament such as a freeze-dried medicament dislikes moisture, if a filling/discharge port is provided in a powdered medicament containing chamber, there is a risk that moisture enters the interior through the filling/discharge port. There is also a risk that the powdered medicament may not be completely dissolved in the liquid if the powdered medicament adheres to the interior of the filling/discharge port. However, there are such advantages that the liquid medicament can be supplied through the filling/discharge port when manufactured since the filling/discharge port is provided in the liquid-medicament containing chamber, and that its liquid level can be visually checked during use since the liquid-medicament containing chamber is generally transparent.

However, in the above-mentioned prior-art container in which the filling/discharge port is provided in the liquid-medicament containing chamber, only a liquid medicament is administered to a patient when a user forgets bringing the liquid-medicament containing chamber into communication with a powdered medicament in a medical situation. In this case, re-administration must be performed with a new bag, and a powdered medicament which is expensive compared to a dissolving solution must be discarded. In addition, the emergency characteristic of the plural-chamber bag which is the greatest advantage thereof is impaired, and a patient suffers from excess pain.

To solve these problems, a plural-chamber bag has been proposed in which a space is provided between a filling/discharge port and a liquid-medicament containing chamber via a weakly sealed portion, and when a liquid-medicament containing chamber is pressed during use, a weakly sealed portion between the powdered medicament containing chamber and the liquid-medicament containing chamber allows communication therebetween and then the weakly sealed portion in front of the filling/discharge port allows communication with the liquid medicine (Japanese unexamined patent publication No. 9-327498). Accordingly, even if administration is to be performed during a non-communicated state, the problem that only the liquid medicament is administered is avoided since the weakly sealed portion is provided between the filling/discharge port and the liquid medicament.

However, in the invention described in Japanese unexamined patent publication No. 9-327498, the interior of the space provided via a weakly sealed portion and the interior of the filling/discharge port cannot be sterilized even with high-pressure steam sterilization because no moisture at all exists in the space in front of the filling/discharge port. In this publication, it is stated in lines 31–34 in the right column of page 3, that a physiological salt solution may be contained in the space. In this case, there is a need for a step of charging a liquid other than a liquid medicament into the space, so that the manufacturing process becomes complicated. In addition, since the container becomes long owing to the provision of the space in front of the filling/discharge port, the space becomes obstructive during safekeeping. The container is generally packed in the state of being folded at the partitioning portion in order to prevent accidental communication during safekeeping in the weakly sealed portion in particular. Accordingly, the weakly sealed portion in front of the filling/discharge port must be folded, so that the packaging process becomes complicated and there is a risk that the package size (particularly, thickness) becomes large.

Namely, a problem to be solved by the present invention is to provide a construction which is provided with an absolutely safe mechanism (a so-called fail safe mechanism) which does not allow an administration-without-communication operation in order to prevent a medical container containing a plurality of medicaments which are to be mixed during use from being used in a non-communicating state, as well as which can use an existing manufacturing process and is the same in size as existing constructions.

SUMMARY OF THE INVENTION

To solve the above-mentioned problem, the present inventor has made intensive research and reached the present invention. Namely, the present invention relates to the following filling/discharge port and medical container:

(1) A displaceable-plug-containing filling/discharge port includes;

an approximately cylindrical port cap which is opened at its distal end and its proximal end;

a container port which is fitted into the proximal end of the port cap;

a plug which is hermetically and longitudinally slidably fitted in an inside of the port cap; and a plug cap which is removably fitted to a tip of the plug, the plug and the plug cap being integrally combined, a tip of the plug cap being displaceable from a closed position where the tip of the plug cap is positioned closer to a proximal end than the tip of the port cap to a discharge position where the plug cap projects from the port cap in its distal end direction.

(2) The displaceable-plug-containing filling/discharge port as in (1), wherein when a pressure on a proximal end side of the plug is increased, the plug cap is displaced from the closed position to the discharge position by this pressure.

(3) The displaceable-plug-containing filling/discharge port as in (1) or (2) which further includes in the port, a proximal stopper which prevents the plug from being displaced in the proximal end direction of the port cap when the plug is at the closed position.

(4) The displaceable-plug-containing filling/discharge port as in any of (1) to (3) which further includes in the port cap, a distal stopper which prevents the plug from being displaced in the distal end direction of the port cap when the plug is at the discharge position.

(5) The displaceable-plug-containing filling/discharge port as in any of (1) to (4) which further includes an engagement means which provides an engagement between the plug and the port cap with each other when the plug is at the discharge position.

(6) The displaceable-plug-containing filling/discharge port as in (5), wherein the engagement means includes a depressed groove circumferentially provided in an outer circumferential surface of the plug and a projecting ridge circumferentially provided in an inner circumferential surface of the port cap.

(7) The displaceable-plug-containing filling/discharge port as in any of (1) to (6), wherein the plug is an elastic member which is hermetically and longitudinally slidably fitted in the inside of the port cap.

(8) The displaceable-plug-containing filling/discharge port as in (7), wherein a distance L1 from the proximal end of the distal stopper to the tip of the plug at the closed position is shorter than a longitudinal length L2 of the plug, and a seal portion which is positioned closest to the proximal end of the plug at the discharge position is positioned closer to the proximal end than the seal portion which is positioned closest to the tip of the plug at the closed position.

(9) A medical container provided with the displaceable-plug-containing filling/discharge port as in any of (1) to (8), wherein a plurality of medicaments are contained in a plurality of chambers partitioned via a partitioning portion which allows communication therebetween when an internal pressure in a chamber of the container is increased by pressure applied from outside the container.

(10) The medical container as in (9), wherein the plug is slid from the closed position to the discharge position when the internal pressure is increased by pressure applied from outside the container.

(11) The medical container as in (9) or (10), wherein a container body is a bag made of a thermoplastic sheets, and the partitioning portion is formed by weakly melt-bonding the sheets which form the container body, or has a construction in which the container body sheets are bonded to each other via a heat-sealable sheet.

(12) The medical container as in (9) or (10), wherein the container body is a soft resilient bottle.

(13) The medical container as in any of (9) to (12), wherein at least one of the medicaments is a liquid medicament.

(14) The medical container as in (13), wherein the chamber containing the medicament is provided with the filling/discharge port.

(15) The medical container as in (14), wherein the plug is slid from the closed position to the discharge position by an internal pressure higher than an internal pressure which causes the partitioning portion to rupture and the insides of the chambers to allow communication.

BRIEF DESCRIPTION OF THE DRAWINGS

FIG. 1(*a*) is a longitudinal sectional view showing a closed position, while FIG. 1(*b*) is a longitudinal sectional view showing a discharge position.

FIG. 3(*a*) is a longitudinal sectional view showing the closed position, while FIG. 3(*b*) is a longitudinal sectional view showing the discharge position.

FIG. 4(*a*) is a longitudinal sectional view showing the closed position, FIG. 4(*b*) is a longitudinal sectional view showing the discharge position, and FIG. 4(*c*) is a cross-sectional view taken along line C-C (the container is not shown).

FIG. 5(*a*) is a longitudinal sectional view showing the closed position, while FIG. 5(*b*) is a longitudinal sectional view showing the discharge position.

FIG. 6(*a*) is a longitudinal sectional view showing the closed position, while FIG. 6(*b*) is a longitudinal sectional view showing the discharge position.

Figures 1A, 1B:
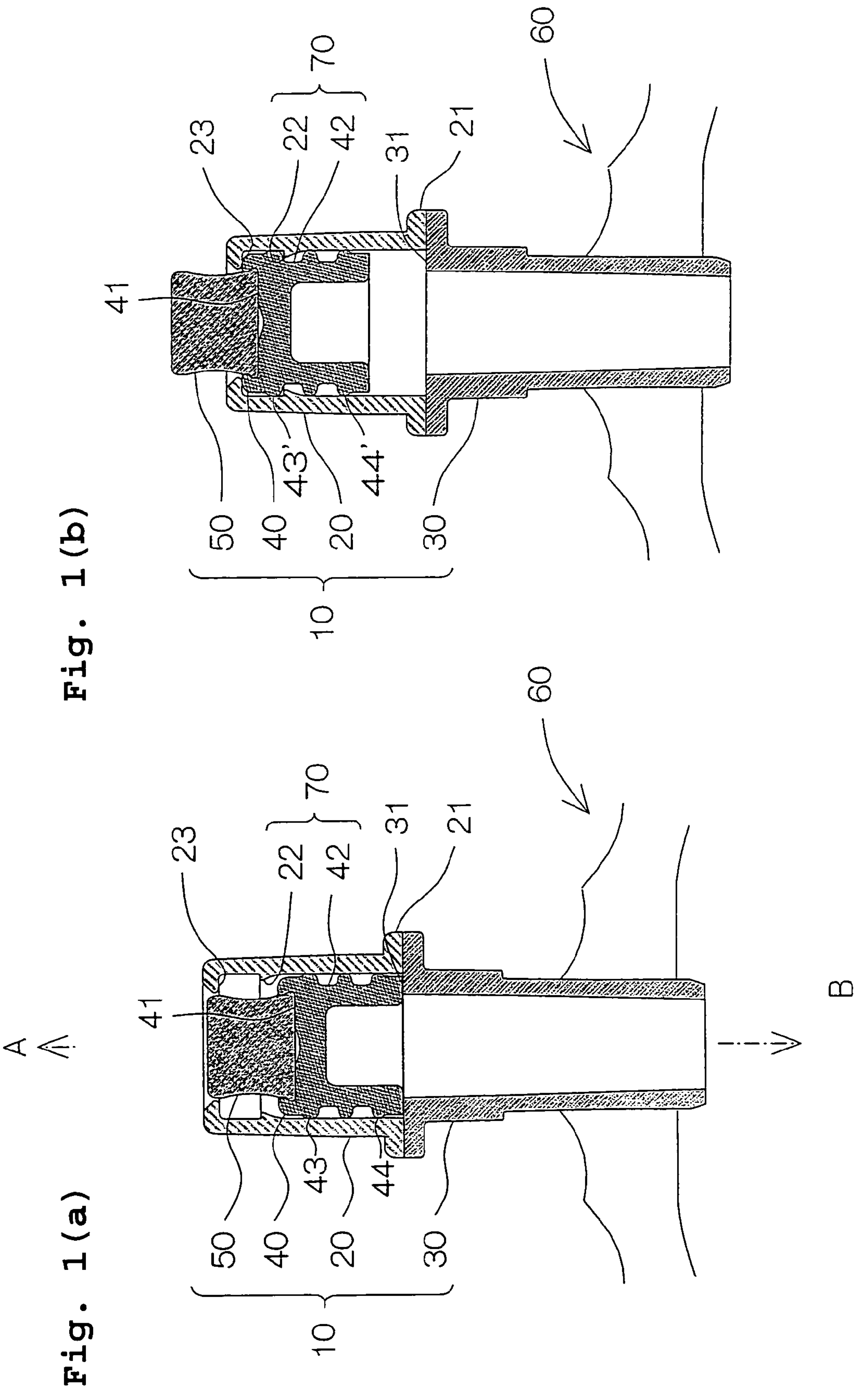
FIG. 1 is a longitudinal sectional view showing an embodiment of a filling/discharge port of the present invention.

In the present specification, the term “distal end direction” denotes the direction of arrow A in the drawing, and the term “proximal end direction” denotes the direction of arrow B in the drawing.

DETAILED DESCRIPTION OF THE INVENTION

Embodiments of the present invention will be described below with reference to the accompanying drawings.

First, one embodiment of a displaceable-plug-containing filling/discharge port of the present invention will be described below with reference to FIGS. 1(*a*) and 1(*b*) (first embodiment). A displaceable-plug-containing filling/discharge port 10 of the present invention, as shown in FIGS. 1(*a*) and 1(*b*), includes an approximately cylindrical port cap 20 which is opened at its distal end and its proximal end, a port 30 which is fitted to the proximal end of the port cap 20, a plug 40 which is hermetically and longitudinally slidably fitted in the inside of the port cap 20, and a plug cap 50 which is removably fitted to the tip of the plug 40.

The approximately cylindrical port cap 20 which is opened at its distal end and its proximal end is provided at the distal end of the port 30 and is usually made of an artificial resin or the like, and has a length and diameter that are selected depending on the ingredients in the medical container and the rate of filling/discharging of the ingredients into/from the container but are not limited in the present invention. The port 30 which is provided at the proximal end of the port cap 20 is usually made of an artificial resin or the like, and is joined with the port cap 20 by a flange. The port 30 is joined to the tip of the container body 60 or integrated with the container body 60. The plug 40 which is hermetically and longitudinally displacably fitted in an inside of the port cap 20 is usually made of thermoplastic elastomers or rubbers and usually includes a top plate, a cylindrical plug leg and seal portions contacting with the port 30, and thickness of the top plate, and a diameter or length of the cylindrical leg are properly selected depending on the inner diameter of the port cap 20 and the like. Further, the plug 40 and the port cap 20 have an engagement means 70 and seal portions 43 and 44 in the closed state. The engagement means 70 includes a depressed groove 42 circumferentially provided in the outer circumferential surface of the plug 40 and a projecting ridge 22 circumferentially provided in the inner circumferential surface of the port cap 20. The seal portions are for hermetically sealing the portion between the plug 40 and the port cap 20 and include circular projecting portions of the plug 40 which contact the inner surface of the port cap 20. Usually, the plug 40 has a plurality of circular projecting portions which are provided around the periphery of the plug 40. In FIG. 1(*a*), the most distal seal portion 43 and the most proximal seal portion 44 in the closed state are shown.

An injection needle, a mixing needle, a connecting needle or the like is stuck from the top plate of the plug 40 during use. The tip of the plug 40 and the proximal end of the plug cap 50 are preferably, hermetically fitted to each other in the state of being removable with a hand, a finger or the like. As a fitting method, as shown in FIGS. 1(*a*) and 1(*b*), a depressed portion 41 into which an enlarged-diameter portion of the proximal end of the plug cap 50 fits may be provided at the tip of the plug 40, or screwing threads (not shown) which mate with each other may be provided at the tip of the top plate of the plug 40 and at the proximal end of the plug cap 50. These plug 40 and plug cap 50 integrally slide from a closed position where the tip of the plug cap 50 does not protrude from the tip of the port cap 20 as shown in FIG. 1(*a*) to a discharge position where the plug cap 50 projects from the port cap 20 in its distal end direction as shown in FIG. 1(*b*). The sliding of the plug 40 is performed by pressure applied on the proximal end side of the plug 40. The pressure applied on the proximal end side can release the connection between the inner peripheral surface of the port 30 and the seal portions 43 and 44 in the plug 40 in the closed state and cause the plug cap 50 to protrude from the tip of the port cap 30. The pressure varies depending on an inner peripheral surface of the port 30 and the material, surface condition, or contacting area of the plug 40 and the like. Usually, the pressure is preferably, applied by pressing the outer surface of the container body 60 by hand which is connected with the port 30.

At the closed position (a), the tip of the plug cap 50 does not protrude from the tip of the port cap 20 and the tip of the plug cap 50 cannot be picked up with fingertips or the like, so that the plug cap 50 cannot be removed from the plug 40. It is to be noted that, at the discharge position (b), since the plug cap 50 projects in the distal end direction of the port cap 20, the plug cap 50 can be easily removed from the plug 40.

The proximal end of the port cap 20 forms a flange 21, and this flange 21 is hermetically melt-bonded to the tip of the port 30 provided in a container body 60. The inner diameter of the proximal end of the port cap 20 is made slightly larger than the inner diameter of the tip of the port 30. This forms a proximal stopper 31 which, when the plug 40 is at the closed position (a), prevents this plug 40 from sliding further in the proximal end direction. The connection between the proximal end of the port cap 20 and the distal end of the port 30 is not limited to a flange.

A tip circumferential portion of the port cap 20 is diametrically reduced, in part or in whole, toward the center thereof, and forms a distal stopper 23 which, when the plug 40 fitted inside is at the discharge position (b), prevents this plug 40 from sliding further in the distal end direction.

In addition, the port cap 20 and the plug 40 are provided with engagement means 70 which prevents the plug 40 from sliding in the proximal end direction when, for example, an injection needle is stuck into the plug plate top of the plug 40 positioned at the discharge position (b) and a force causing the plug 40 to slide in the proximal end direction acts on the plug 40. As the engagement means 70, a depressed groove 42 circumferentially provided in the outer circumferential surface of the plug 40 and a projecting ridge 22 circumferentially provided in the inner circumferential surface of the port cap 20 are adopted. In this case, the depressed groove 42 needs to be provided around the entire outer circumferential surface of the plug 40, whereas the projecting ridge 22 need not necessarily to be provided around the entire circumference and may be provided on a part thereof as long as the projecting ridge 22 can prevent the plug 40 positioned at the discharge position (b) from sliding in the proximal end direction. It is to be noted that the tip side of the projecting ridge 22 preferably has a flat surface. Accordingly, the plug 40 positioned at the discharge position is far more reliably prevented from easily sliding in the proximal end direction. It is also to be noted that the number of depressed grooves 42 provided in the outer circumference of the plug 40 need not be one and a plurality of depressed grooves 42 may also be provided in the longitudinal direction. Accordingly, the area of contact between the plug 40 and the port cap 20 can be decreased to improve slidability.

Figure 2B:
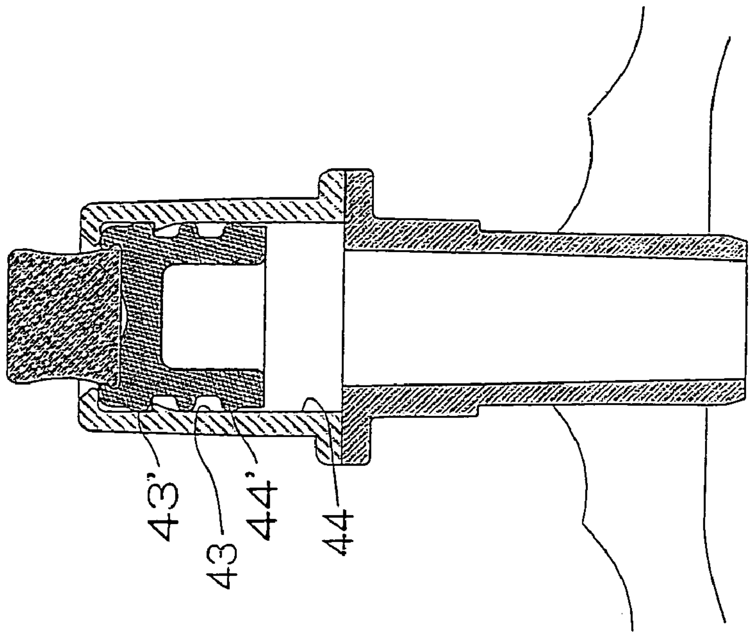
FIG. 2 is a longitudinal sectional view showing a distance from the proximal end of the distal stopper in the filling/discharge port to the tip of the plug and a longitudinal length of the plug shown in FIG. 1, and a relative situation of the seal portion of the plug in the closed position (a) in FIG. 2(*a*) to the seal portion of the plug in the discharge position (b) in FIG. 2(*b*).
Figure 2A:
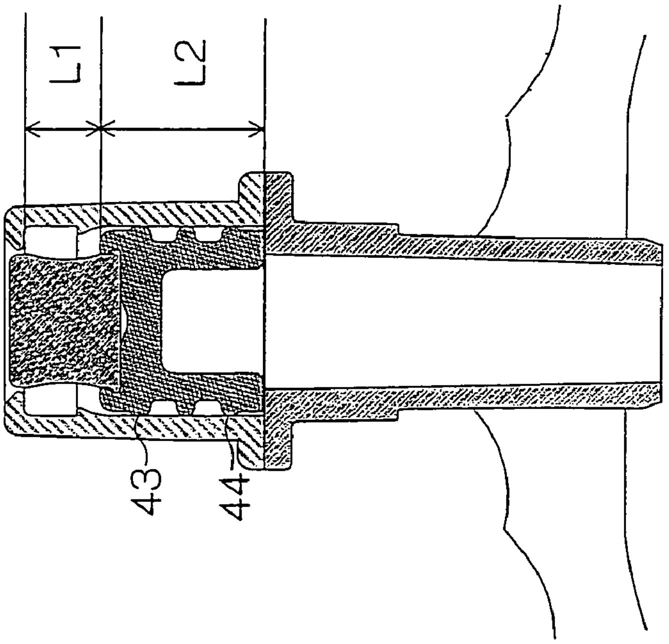

When plug cap 50 is at the closed position (a), the outside air passes through the gap between the outer circumferential edge of the plug cap 50 and the inner circumferential edge of the port cap 20, and the proximal end of the distal stopper 23 and the tip of the plug plate of the plug 40 are exposed to the outside air. As a result, the asepsis of this portion cannot be ensured. For this reason, in order to prevent a portion exposed to the outside air and a medicament inside a medical container from coming into contact with each other when the plug 40 slides to the discharge position (b), the distance L1 from the proximal end of the distal stopper 23 to the tip of the plug plate of the plug 40 at the closed position (a) is made shorter than the longitudinal length L2 of the plug 40 (refer to FIG. 2(*a*)). The seal portion 44' which is positioned closest to the proximal end of the plug 40 at the discharge position (b) is positioned closer to the proximal end than the seal portion 43 which is positioned closest to the tip of the plug 40 at the closed position (a)(refer to FIG. 2(*b*)). The seal portions in the closed position (a) are seal portion 43 positioned in the most proximal end of the plug 40 and seal portion 44 positioned in the most distal end of the plug 40.

The seal portions in the discharge position (b) are seal portion 43' positioned in the most proximal end of the plug 40 and seal portion 44' positioned in the most distal end of the plug 40. The number of the seal portions is not limited.

Another embodiment of a displaceable-plug-containing filling/discharge port of the present invention will be described below with reference to FIGS. 3(*a*) and 3(*b*) (second embodiment). The port, the plug and the plug cap in FIG. 3 are similar to those in FIGS. 1 and 2.

Figure 3B:
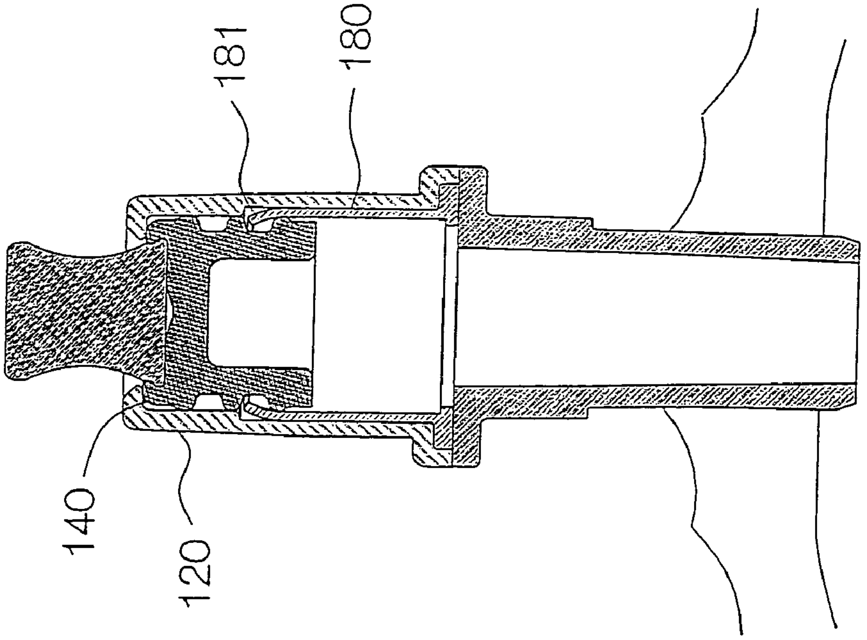
FIG. 3 is a longitudinal sectional view showing another embodiment of a filling/discharge port of the present invention in which a collar for surrounding a plug is provided in the interior of a port cap.
Figure 3A:
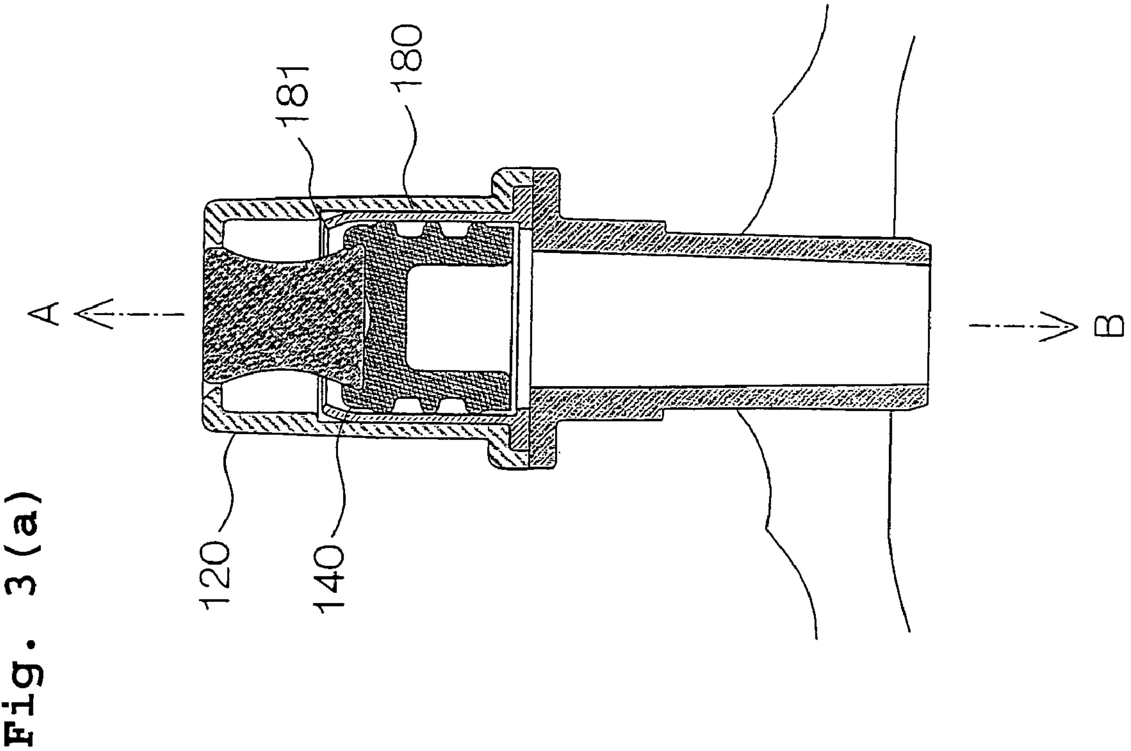

In the case where a projecting ridge is not provided on the inner circumferential surface of a port cap, a collar 180 which surrounds a plug 140 may be fitted into a port cap 120 as shown in FIGS. 3(*a*) and 3(*b*) in order to hold the plug 140, and a tapered portion 181 which serves a function and an advantage similar to those of the above-mentioned projecting ridge 22 may be provided on the inner circumferential surface of this collar 180.

Otherwise, a collar 180 in which a plug 140 formed of a thermoplastic elastomer or the like is previously secured by blocking may be fitted in a port cap 120. The term "blocking" denotes the phenomenon in which the plug 140 made of a thermoplastic elastomer, a silicone elastomer or butyl rubber and the port cap 120 made of a polyolefin resin closely adhere to each other and becomes resistant to separation from each other, and by variously changing the conditions of blocking such as the materials of the plug 140 and the port cap 120, it is possible to control the sliding initial pressure at which the plug starts sliding. Incidentally, in this case, a projecting ridge may, of course, be provided in the collar 180, but the sliding initial pressure may also be controlled only by the above-mentioned blocking without the projecting ridge.

Yet another embodiment of a displaceable-plug-containing filling/discharge port of the present invention (third embodiment) will be described below with reference to FIGS. 4(*a*) and 4(*b*). The port, the plug and the plug cap in FIG. 4 are similar to those in FIGS. 1 and 2.

Figures 4A, 4B, 4C:
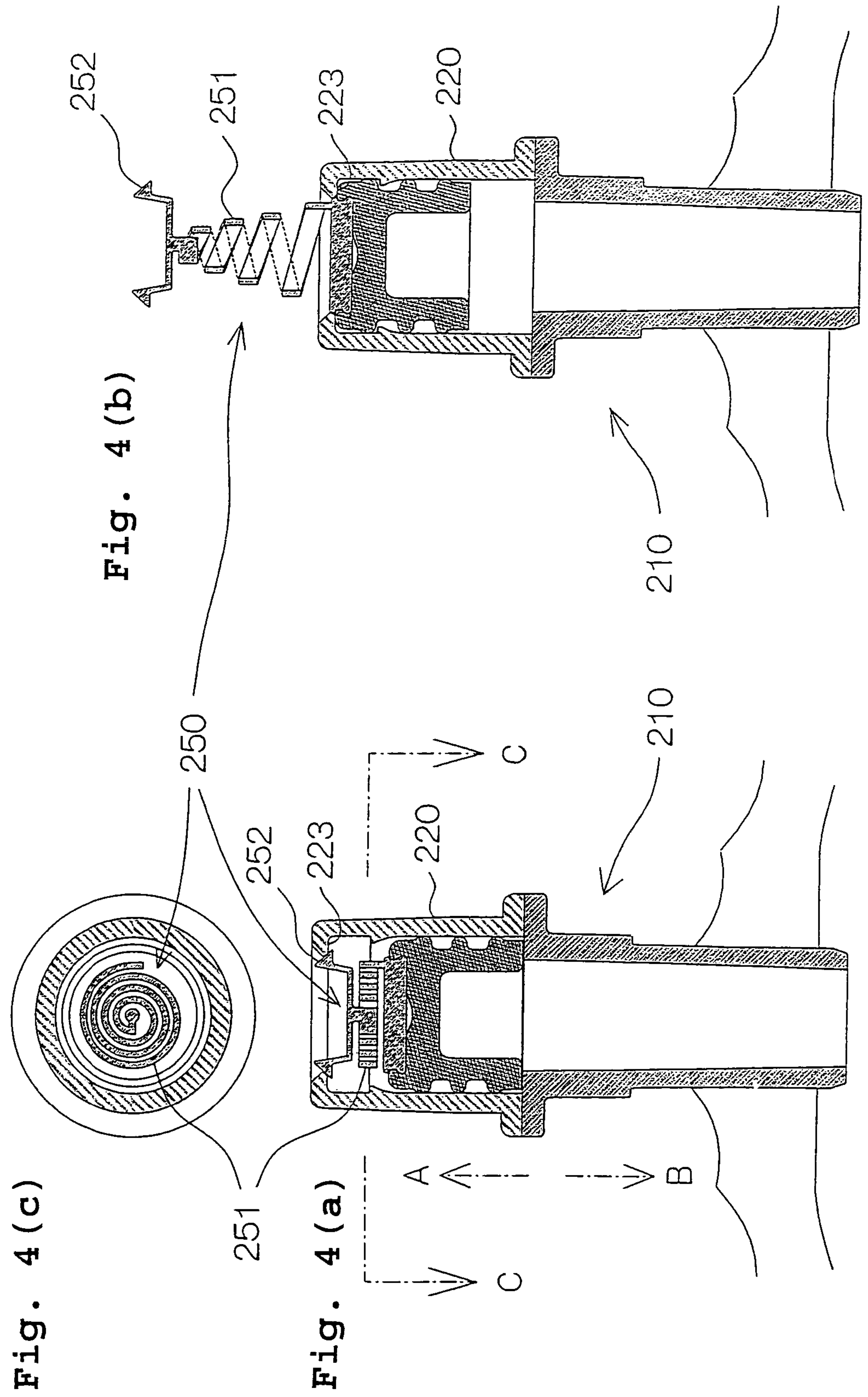
FIG. 4 is a longitudinal sectional view showing another embodiment of a filling/discharge port of the present invention in which a plug cap is an expansible plug cap.

The displaceable-plug-containing filling/discharge port 210 shown in FIGS. 4(*a*) and 4(*b*) has a plug cap formed as an extensible plug cap 250 having elasticity in the longitudinal direction so as to extend in the distal end direction when the plug cap is at the discharge position (b). By lifting the tip portion of the extensible plug cap 250 at the discharge position (b), the removal of the plug cap 250 becomes far easier. A spiral spring 251 having elasticity in the longitudinal direction is provided in the middle portion of the extensible plug cap 250, and a flexing portion 252 which can flex toward the center is provided at the tip of the spiral spring 251. The tip of the flexing portion 252 is brought in engagement with a distal stopper 223 of a port cap 220 at the closed position, and the flexing portion 252 flexes toward the center when a force acts in the distal end direction, and is released from the engagement. The extensible plug cap 250 released from engagement is extended in the distal end direction by its elastic force, and is removed by the flexing portion 252 or the extended spiral spring 251 being lifted.

Yet another embodiment of a displaceable-plug-containing filling/discharge port in the present invention (fourth embodiment) will be described below with reference to FIGS. 5(*a*) and 5(*b*).

Figures 5A, 5B:
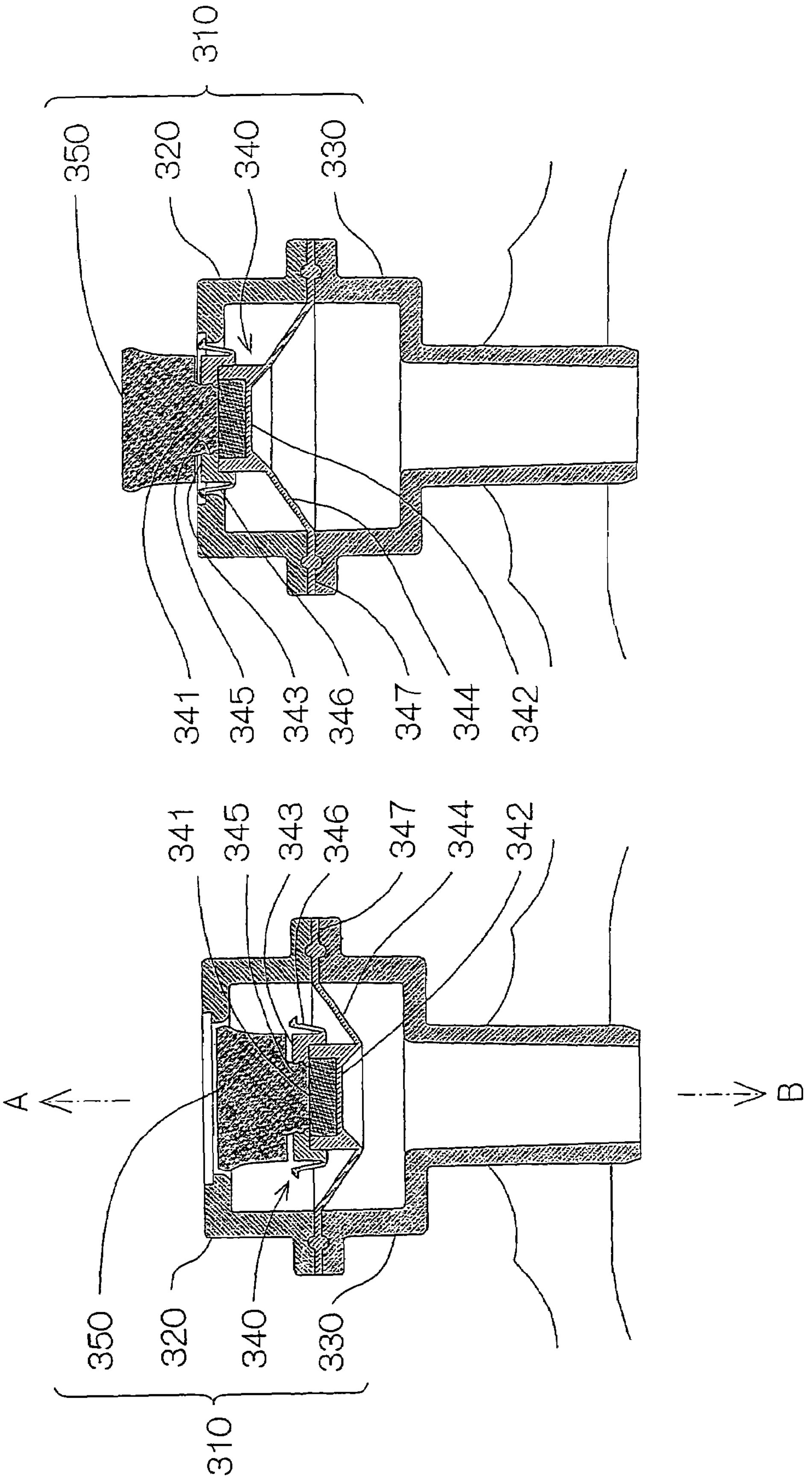
FIG. 5 is a longitudinal sectional view showing another embodiment of a filling/discharge port of the present invention in which the plug is of the diaphragm type.

The displaceable-plug-containing filling/discharge port 310 shown in FIGS. 5(*a*) and 5(*b*) is of the diaphragm type in which a plug 340 is displaceable in the longitudinal direction. This plug 340 includes a cylindrical elastic member 341 into which a needle can be stuck, a housing portion 342 which concentrically holds this elastic member 341, a housing cap 343 put on the housing portion 342, a tapered portion 344 provided obliquely radially from the outer circumference of the housing portion 342, and a flange 347 provided on the outer circumference of the tapered portion 344, and in the case where a force is applied from the proximal end direction toward the distal end direction, the tapered portion 344 is warped, whereby the housing portion 342 becomes displaceable in the longitudinal direction.

A plug cap 350 is removably fitted to the housing cap 343 and both are engaged in an engagement portion 345. An engagement claw 346 capable of flexing in its radial directions is provided on the outer circumference of the housing cap 343, and the engagement claw 346, when it is at the discharge position (b) shown in FIG. 5(*b*), engages with the inner circumference of the tip of the port cap 320, thereby preventing the displacement of the housing portion 342 in the proximal end direction.

Flange 347 is hermetically adhered or melt-bonded to the distal end of a port 330 and the proximal end of the port cap 320.

Yet another embodiment of a displaceable-plug-containing filling/discharge port of the present invention (fifth embodiment) will be described below with reference to FIGS. 6(*a*) and 6(*b*).

Figure 6B:
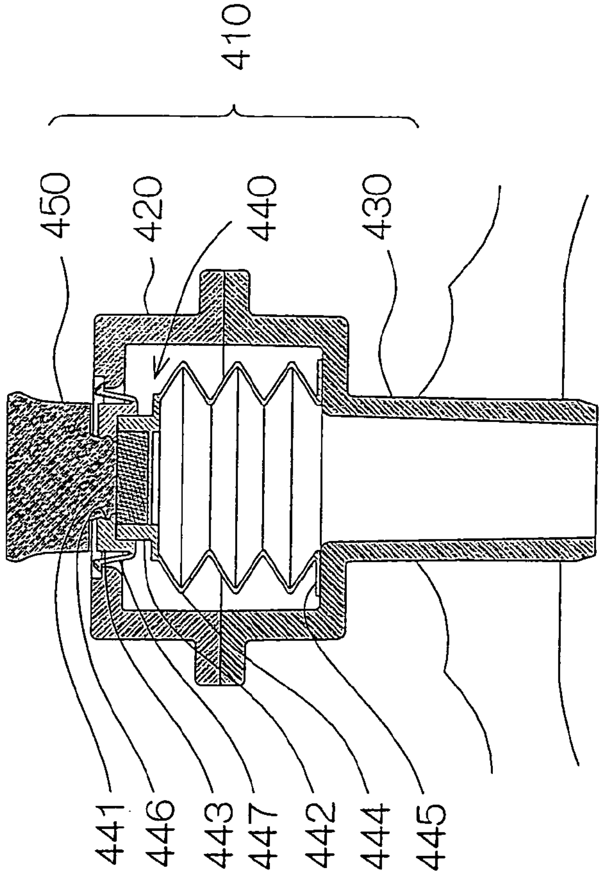
FIG. 6 is a longitudinal sectional view showing an embodiment of a filling/discharge port of the present invention in which the cap is of the bellows type.
Figure 6A:
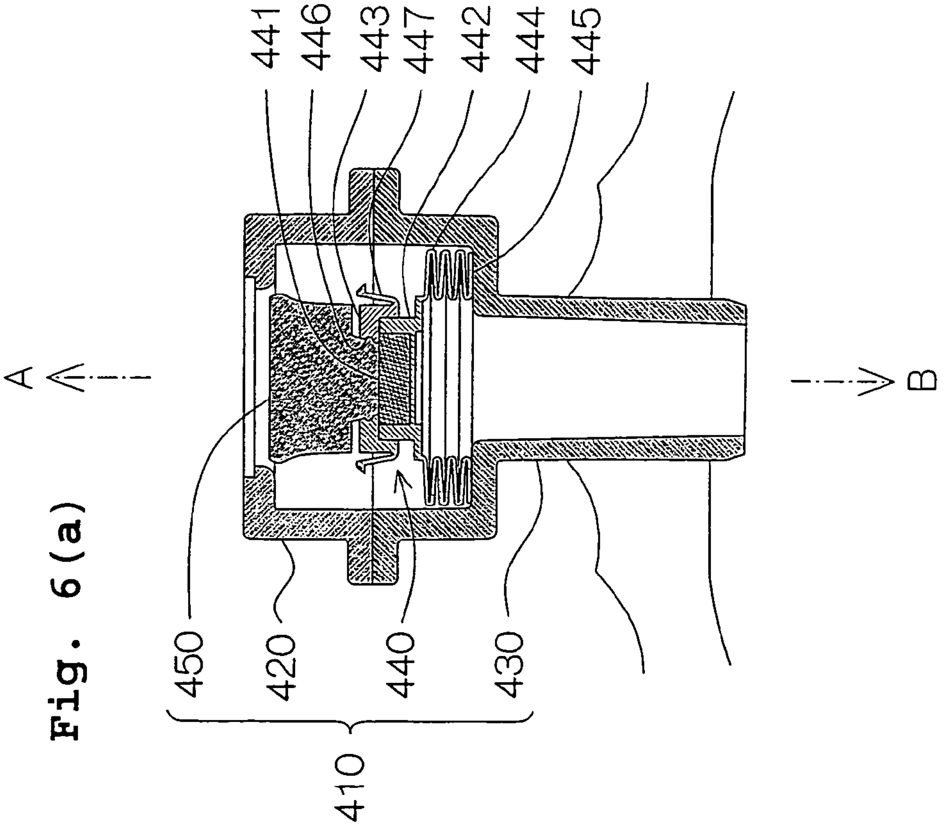

The displaceable-plug-containing filling/discharge port 410 shown in FIGS. 6(*a*) and 6(*b*) is of the bellows type in which a plug 440 is expansible in the longitudinal direction. This plug 440 includes a cylindrical elastic member 441 into which a needle can be stuck, a housing portion 442 which concentrically holds this elastic member 441, a housing cap 443 put on the housing portion 442, a bellows portion 444 provided from the outer circumference of the housing portion 442 in the proximal end direction, and a flange 445 provided on the outer circumference of the bellows portion 444, and when a port cap 420 is at the closed position shown in FIG. 6(*a*), the bellows portion 444 is shrunk or contracted, and in the case where a force is applied from the proximal end direction toward the distal end direction, the bellows portion 444 is expanded as shown in FIG. 6(*b*) and the housing portion 442 is displaced in the longitudinal direction.

A plug cap 450 is removably fitted to the housing cap 443 and both are engaged in an engagement portion 446. An engagement claw 447 capable of flexing in its radial direction is provided on the outer circumference of the housing cap 443, and this engagement claw 447, when it is at the discharge position shown in FIG. 6(*b*), engages with the inner circumference of the tip of the port cap 420, thereby preventing the displacement of the housing portion 442 in the proximal end direction.

The port cap 420 is connected with a port 430 by means of flanges thereof. The port 430 has a construction of two cylindrical parts, large and small, and a connecting part between the cylindrical parts which forms a step. A flange 445 of the bellows portion 444 is hermetically adhered or melt-bonded to the step portion of the port 430.

The forming material of each of the port caps 20, 120, 220, 320 and 420 of embodiments 1 to 5 includes polyethylene, polypropylene, polyethylene terephthalate, polyethylene naphthalate, polyvinyl alcohol, ethylene-vinyl alcohol copolymer, polyvinylidene chloride and nylon as well as mixtures thereof, or layered structures of them, and the kinds of forming materials are not particularly limited as long as they are known for use as forming materials of medical containers.

As the forming material of each of the plugs 40 and 140 in embodiments 1 to 3 and the elastic members 341 and 441 in embodiments 4 and 5, elastic materials are enumerated such as butyl rubber, chlorinated butyl rubber, thermoplastic elastomers and silicone elastomers, and the kinds of forming materials are not particularly limited as long as they are known for use as forming materials of medical containers. Each of the plugs 40 and 140 in embodiments 1 to 3 may be laminated with a film of polyethylene, polypropylene, Teflon (registered trademark) or the like in order to prevent medicament degradation due to contact with solutions, or may also be made of two layers using isoprene rubber. The top plates of the plugs 40 and 140 are depressed toward the center of the top plates by reducing the wall thickness. Accordingly, it is possible to prevent coring when an injection needle or the like is stuck, and when an injection needle is to be forcedly stuck into the plugs, the thin-walled portion disperses this force, whereby it is possible to prevent the plug from coming off into the interior of a container, and it is possible to reduce the cost of components.

As the forming material of each of the plugs 340 and 440, excluding the elastic members 341 and 441, polyethylene, polypropylene, polystyrene, polycarbonate, polyvinyl chloride, nylon and the like are enumerated, and any kind of semi-rigid plastic can be suitably adopted, and elastic materials such as butyl rubber, chlorinated butyl rubber, thermoplastic elastomers and silicone elastomers may also be used.

As the forming material of each of the plug caps 50, 250, 350 and 450 in embodiments 1 to 5, polyethylene, polypropylene, polystyrene, polycarbonate, polyvinyl chloride, nylon and the like are enumerated, and any kind of semi-rigid plastic can be suitably adopted.

Figure 7:
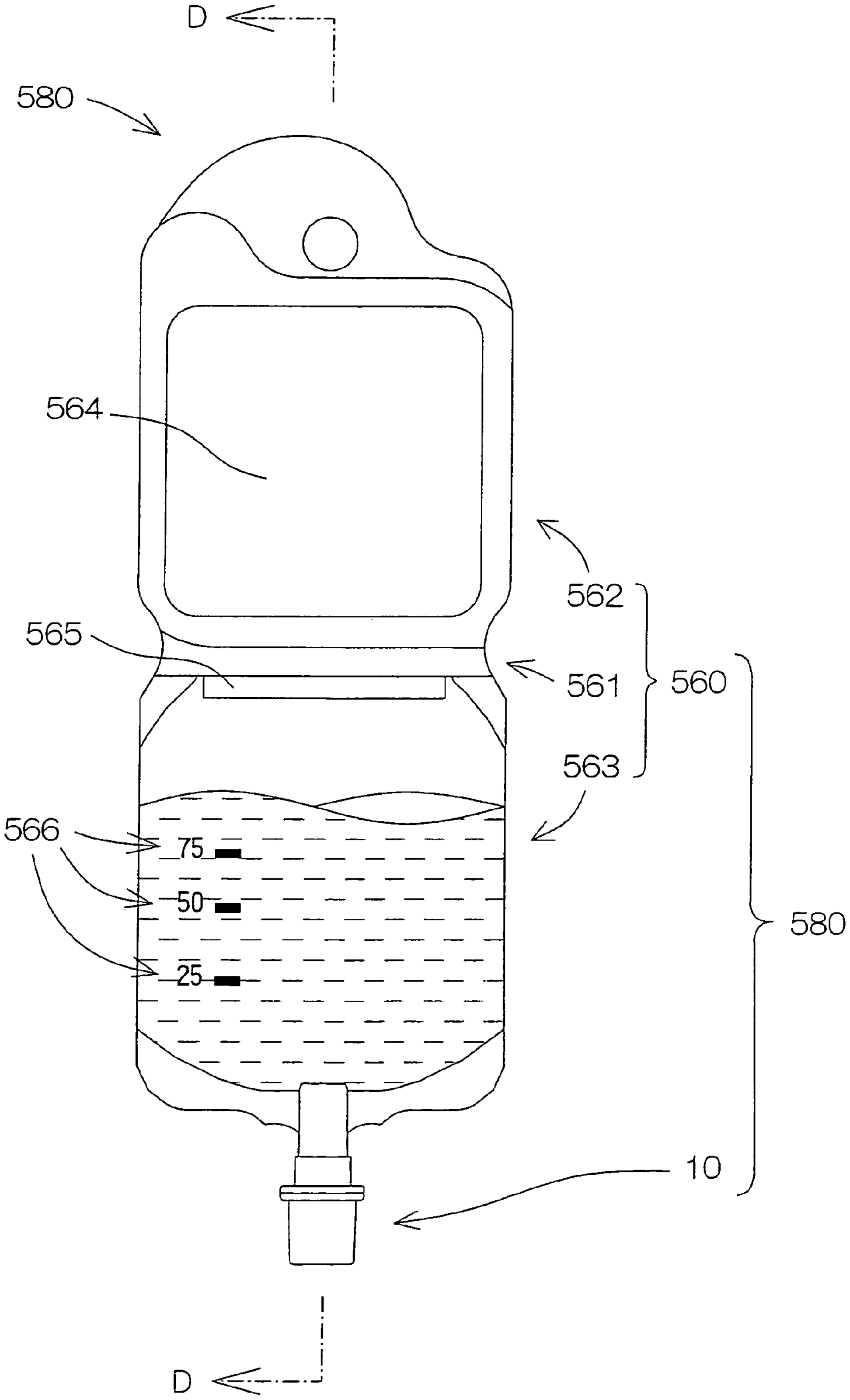
FIG. 7 is a front view showing an embodiment of a medical container of the present invention.
Figure 8:
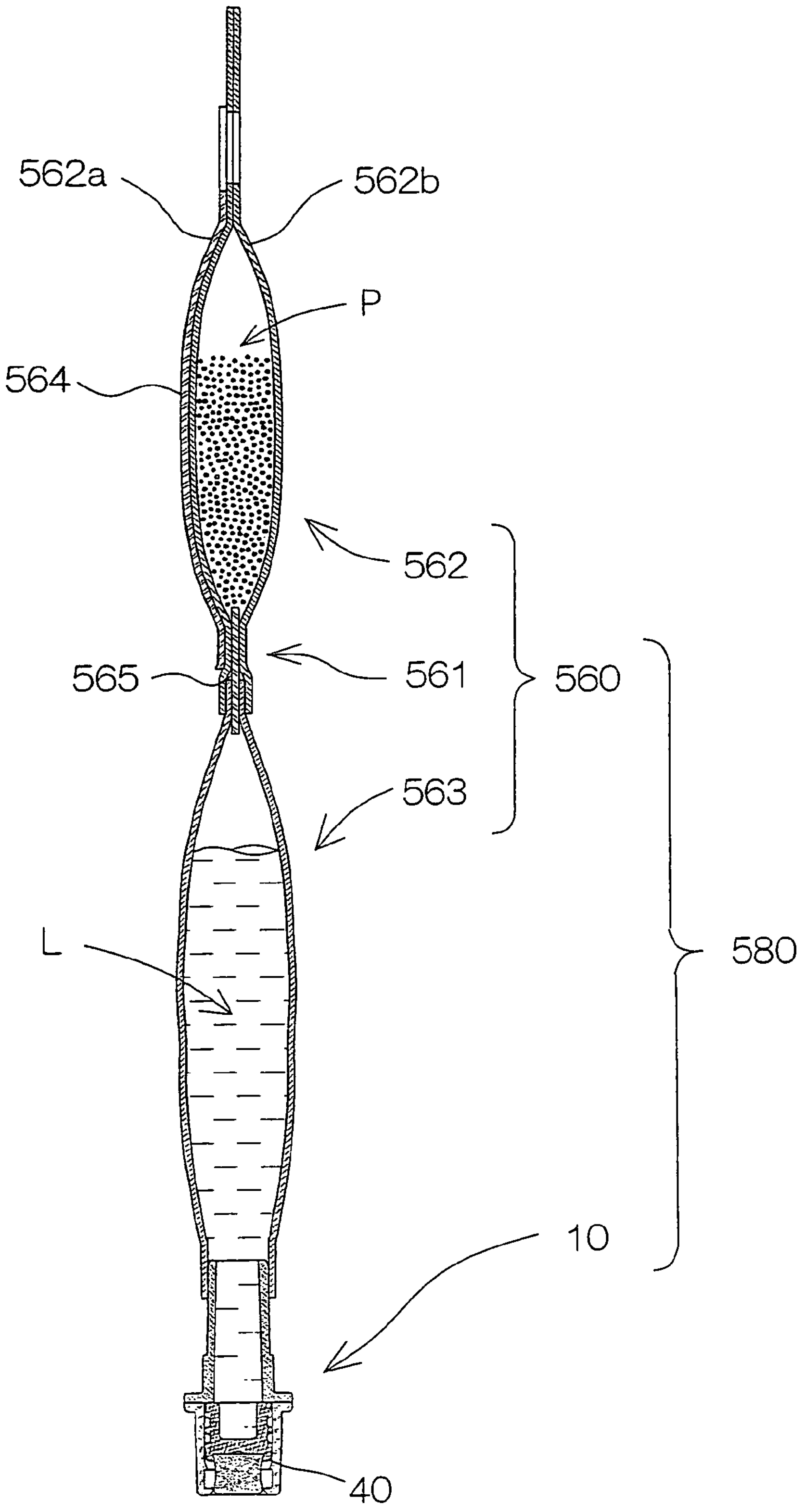
FIG. 8 is a front cross-sectional view, taken along line D—D, of the medical container of the present invention shown in FIG. 7.

Next, an embodiment of a medical container provided with a displaceable-plug-containing filling/discharge port of the present invention will be described with reference to FIGS. 7 and 8. The medical container 580 of the present invention shown in FIGS. 7 and 8 includes a container body 560 which is partitioned into a first medicament containing chamber 562 and a second medicament containing chamber 563 by a partitioning portion 561 which allows communication therebetween when internal pressure in chamber 563 is increased by pressure being applied from outside the container, and a displaceable-plug-containing filling/discharge port in the present invention which is provided in one of the chambers (in this case, the second medicament containing chamber 563). The medical container 560 of the present invention shown in FIGS. 7 and 8 is provided with the filling/discharge port 10 containing the displaceable-plug shown in FIG. 1.

By increasing the internal pressure by the application pressure from outside the container body 560, it is possible to slide the plug in the filling/discharge port 10 from the closed position to the discharge position. The inner pressure in the chamber 563 which is increased by pressing the container from outside can release the connection between the inner surface of the port and the seal portions in the plug and cause the plug cap to protrude from the tip of the port cap, and a force to release the connection depends on the materials, surface conditions or the contacting area of the port and the plug.

The container body 560 is a bag made of a tube or two sheets made of a thermoplastic resin, and the partitioning portion 561 is formed by weakly bonding the tube or sheets which form the container body 560, or has a construction in which a tube or two sheets which form the container body 560 are melt-bonded to each other via a heat sealable sheet 565. FIGS. 7 and 8 show the latter. In the case where the former is adopted, the partitioning portion is, in general, formed by weakly melt-bonding the middle portion of a bag made from a tube or two sheets which can be melt-bonded to each other.

A liquid medicament L is preferably contained in at least one of the first medicament containing chamber 562 and the second medicament containing chamber 563 (in this case, the second medicament containing chamber 563). This is because it is effectively possible to apply a force to cause the partitioning portion 561 to allow communication and a force to slide the plug 40 by pressure application, from outside, to the second medicament containing chamber 563 which contains the liquid medicament L. In the case where both the first medicament containing chamber 562 and the second medicament containing chamber 563 contain powdered medicaments P, even if the container body 560 is pressed from outside, the partitioning portion 561 has difficulty in allowing communication, and a force to slide the plug 40 is not easily generated. This is because the chambers containing powdered medicaments in many cases have flat shapes containing nearly no spaces, and even if there is a space, the space serves as a cushion. The medicaments contained in the first medicament containing chamber 562 and the second medicament containing chamber 563 may both be liquid medicaments. In addition, the container body 560 may also be further partitioned to have third and fourth medicament containing chambers.

In FIG. 8, a powdered medicament P is contained in the first medicament containing chamber 562, and includes a front sheet 562*a* made of a thermoplastic resin, a rear sheet 562*b* superior in moisture and oxygen blocking performance, and a cover sheet 564 which is weakly bonded to the front sheet 562*a* and superior in moisture and oxygen blocking performance. The portion of the first medicament containing chamber 562 which is connected to the second medicament containing chamber 563 is weakly melt-bonded via a sheet 565 made of a thermoplastic resin which is heat sealable to the front sheet 562*a* and the rear sheet 562*b*. The portion of the first medicament containing chamber 562 which is not connected to the second medicament containing chamber 563 is strongly melt-bonded and difficult to peel apart.

In FIG. 8, the second medicament containing chamber 563 is a transparent bag formed of a sheet made of a thermoplastic resin, and the liquid medicament L is contained in the interior of the second medicament containing chamber 563. The connected portion of the second medicament containing chamber 563 to the first medicament containing chamber 562 is melt-bonded via the weak sealable sheet 565 made of a thermoplastic resin which is heat sealable to sheets of the second medicament containing chamber 563 but easily peeled off. The weakly sealable sheet 565 may be made of the same member as or a different member to the sealable sheet 565 provided in the first medicament containing chamber. When the second medicament containing chamber 563 which contains the medicament is pressed from outside and its internal pressure is increased, the melt-bonding of the partitioning portion 561 is released and the first medicament containing chamber 562 and the second medicament containing chamber 563 are allowed to communicate with each other.

Each of the front sheet 562*a* and the rear sheet 562*b* of the first medicament containing chamber 562 which contains the powdered medicament L preferably has moisture and oxygen blocking performance. The forming material of such sheets includes polyethylene, polypropylene, aluminum-deposited polyethylene terephthalate, silica-deposited polyethylene terephthalate, polyethylene naphthalate, polyvinyl alcohol, ethylene-vinyl alcohol copolymer, polyvinylidene chloride and nylon as well as mixtures, or layered or laminated structures of the above mentioned sheets or aluminum film. Incidentally, in the first medicament containing chamber 562 shown in FIGS. 7 and 8, the cover sheet 564 having moisture and oxygen blocking performance is stuck to the external surface of the front sheet 562*a*, and in this case, no moisture and oxygen blocking performance is required for the front sheet 562*a*. In addition, either one or both of the front sheet 562*a* and the rear sheet 562*b* preferably has transparency.

The forming material of the cover sheet 564 includes aluminum film or sheets such as aluminum-deposited polyethylene, aluminum-deposited polypropylene, aluminum-deposited polyethylene terephthalate, aluminum-deposited polyethylene terephthalate, aluminum-deposited polyethylene terenaphthalate, aluminum-deposited polyvinyl alcohol, aluminum-deposited ethylene-vinyl alcohol copolymer, aluminum-deposited polyvinylidene chloride, aluminum-deposited nylon and the like.

As the forming material of the second medicament containing chamber 563 which contains a liquid medicament, there are sheets made of thermoplastic resins such as polyethylene, polypropylene, polyethylene terephthalate, polyethylene naphthalate, polyvinyl alcohol, ethylene-vinyl alcohol copolymer, polyvinylidene chloride and nylon as well as mixtures, or layered or laminated structures of these thermoplastic sheets, and the kinds of forming materials are not particularly limited as long as they are known for use as forming materials of medical containers. Polyethylene, polypropylene and mixtures of polyethylene and polypropylene can suitably be adopted. The second medicament containing chamber 563 preferably has transparency, because there is a case where a scale 566 for confirming the remaining amount of solution during administration is printed on the surface of the second medicament containing chamber 563, as shown in FIG. 7.

The filling/discharge port 10 of the present invention is preferably provided in the second medicament containing chamber 563 which contains the liquid medicament L. This is because a force to slide the plug in the filling/discharge port 10 can be effectively applied by pressing when the chamber 563 contains the liquid medicament L. In the case where the filling/discharge port 10 of the present invention is provided in the chamber 562 containing a powdered medicament P, even if the chamber 562 containing a powdered medicament P is pressed, not only is the plug 40 difficult to slide, but also the partitioning portion 561 has difficulty in allowing communication. This is because a chamber 562 containing powdered medicaments P in many cases has a flat shape containing nearly no internal spaces, and even if there are spaces, the spaces serve as a cushion.

The communication strength of the partitioning portion 561 and the sliding resistance of the plug are preferably set so that the plug 40 is slid from the closed position to the discharge position by an internal pressure B higher than an internal pressure A which causes the partitioning portion 561 to allow communication. This is because if the plug 40 slides to the discharge position before the partitioning portion 561 allows communication, there is a high risk that the powdered medicament P and the medicament L are not mixed and only the liquid medicament L is administered.

Figure 9:
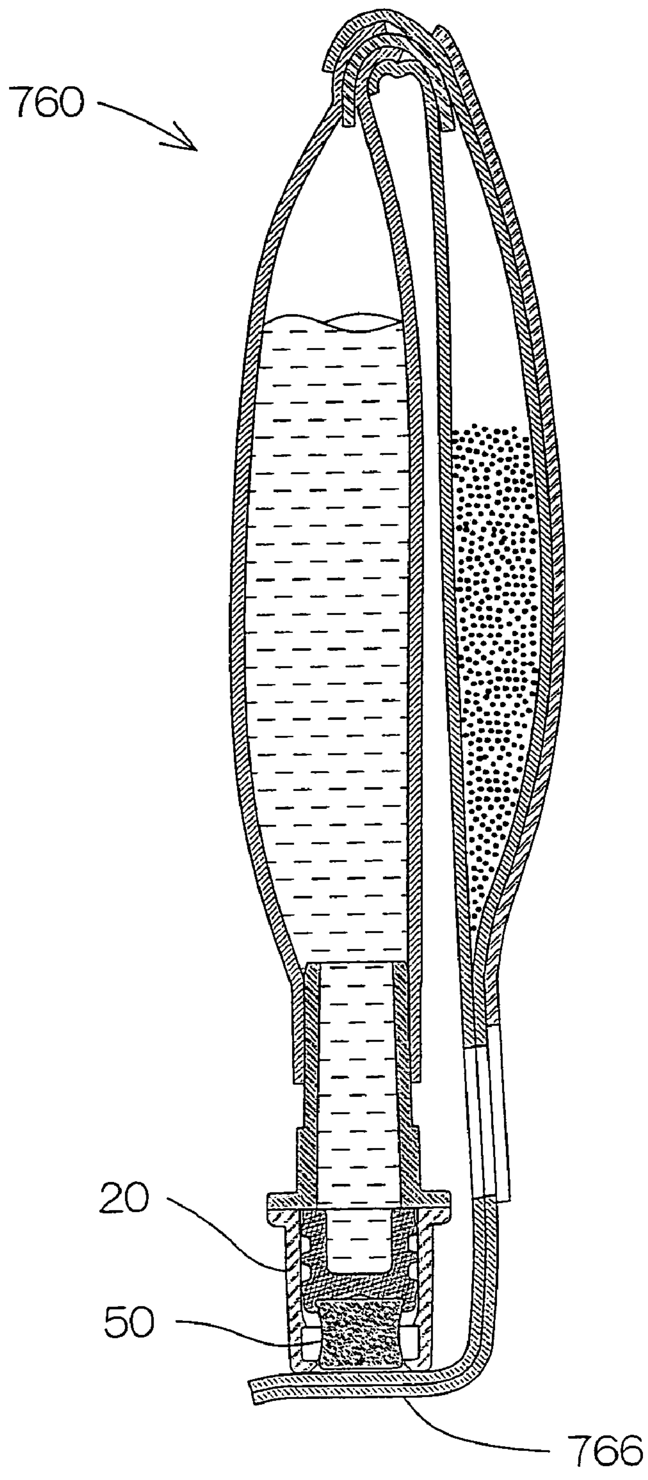
FIG. 9 is a longitudinal sectional view showing the state of safekeeping of another embodiment of a medical container of the present invention, and in FIG. 9, after a container body has been folded, a proximal portion of the container body is melt-bonded to a tip surface of a port cap.

The bag-shaped medicament container having a communicable partitioning portion 561 in its middle portion is packed in the state of being folded at the partitioning portion 561 so that communication is prevented during transportation. Accordingly, even if a considerably large load is applied to the partitioning portion 561, the partitioning portion 561 does not allow communication, but in this case, the plug 40 may occasionally slide to the discharge position. In order to prevent the sliding of the plug 40 during storage, after a container body 760 has been folded as shown in FIG. 9, an end portion 766 of the container body 760 which is close to the tip of the port cap 20 may also be strippably melt-bonded to the tip face of the port cap 20. Incidentally, the melt-bonding strength at this time is set so that the plug cap 50 does not project even when a force to press the folded container body during storage acts on the container.

As is apparent from the foregoing description, in the present invention, in a medical container which contains a plurality of medicaments so that they can be mixed during use, it is possible to reliably prevent the medicaments from being administered to a patient without being mixed by displacement of a tip of a plug cap from a closed position to a discharge position. In addition, since the filling/discharge port of the present invention has an interior in which is accommodated a plug cap which projects outwardly from the filling/discharge port during only discharging, the filling/discharge port differs only in internal structure from medical containers having prior-art filling/discharge ports. Accordingly, by providing the filling/discharge port of the present invention with approximately the same dimensions as prior-art filling/discharge ports, it is possible to manufacture a medical container of the present invention by using an existing manufacturing process, and it is also possible to provide a medical container which is the same in size as existing medical containers.

What is claimed is:

1. A medical container comprising:

a container body provided with a displaceable-plug-containing filling/discharge port;

the displaceable-plug-containing filling/discharge port including;

an approximately cylindrical port cap having a distal end and a proximal end which is opened at the distal end and the proximal end;

a container port to be joined to the container body and which is fitted to the proximal end of the port cap;

a plug which is hermetically and longitudinally slidably fitted in an inside of the port cap; and a plug cap which is removably fitted to a tip of the plug, the plug and the plug cap being integrally combined, a tip of the plug cap being displaceable from a closed position where the tip of the plug cap does not protrude from the distal end of the port cap to a discharge position where the plug cap projects from the distal end of the port cap;

and wherein a plurality of medicaments are contained in the container body in a plurality of chambers partitioned via a partitioning portion which allows communication between the chambers when internal pressure in at least one of the chambers is increased by pressure applied to the container from outside the container.

2. The medical container according to claim 1, wherein the plug is slid from the closed position to the discharge position when the internal pressure inside at least one of the chambers is increased by pressure applied to the container from outside the container.

3. The medical container according to claim 1, wherein the container body is a bag made of a thermoplastic sheets, and the partitioning portion is formed by weakly melt-bonding the sheets which form the container body, or has a construction in which the container body sheets are melt-bonded each to other via a heat sealable sheet.

4. The medical container according to claim 1, wherein the container body is a soft resilient bottle.

5. The medical container according to claim 1, wherein at least one of the medicaments is a liquid medicament.

6. The medical container according to claim 5, wherein the chamber containing the liquid medicament is provided with the filling/discharge port.

7. The medical container according to claim 6, wherein the plug is slid from the closed position to the discharge position by an internal pressure which is higher than an internal pressure which causes the partitioning portion to allow communication.

* * * * *